United States Patent
Kim et al.

(10) Patent No.: US 10,653,396 B2
(45) Date of Patent: May 19, 2020

(54) MULTI-SYNCHRONIZATION POWER SUPPLY AND ULTRASOUND SYSTEM WITH SAME

(71) Applicant: Siemens Medical Solutions USA, Inc., Malvern, PA (US)

(72) Inventors: SeogMin Kim, Seoul (KR); HanSang Ji, Yongin-si (KR)

(73) Assignee: Siemens Medical Solutions USA, Inc., Malvern, PA (US)

( * ) Notice: Subject to any disclaimer, the term of this patent is extended or adjusted under 35 U.S.C. 154(b) by 388 days.

(21) Appl. No.: 15/838,178

(22) Filed: Dec. 11, 2017

(65) Prior Publication Data

US 2018/0168555 A1    Jun. 21, 2018

(30) Foreign Application Priority Data

Dec. 19, 2016 (KR) ............... 20160173390

(51) Int. Cl.
*H02M 3/158* (2006.01)
*A61B 8/00* (2006.01)
*H02M 1/08* (2006.01)
*G01S 7/52* (2006.01)
*H02M 3/00* (2006.01)

(52) U.S. Cl.
CPC ............ *A61B 8/56* (2013.01); *G01S 7/52096* (2013.01); *H02M 1/08* (2013.01); *H02M 3/1584* (2013.01); *H02M 3/00* (2013.01)

(58) Field of Classification Search
CPC ........ G06F 1/26; G06F 1/3203; G06F 1/3296; H02M 3/158; H02M 3/1582; H02M 3/1588; H02M 3/155; H02M 3/156; H02M 3/157; A61B 8/56

USPC .......... 323/271, 282–285; 713/300, 310, 320
See application file for complete search history.

(56) References Cited

U.S. PATENT DOCUMENTS

| | | | |
|---|---|---|---|
| 7,138,788 B2 * | 11/2006 | Rice .................... | H02M 3/1584 323/268 |
| 2011/0234191 A1 * | 9/2011 | Yeon .................... | H02M 3/285 323/285 |
| 2016/0172975 A1 * | 6/2016 | Takeya .................... | H02M 1/08 363/126 |

FOREIGN PATENT DOCUMENTS

| | | |
|---|---|---|
| JP | 2010213787 | 9/2010 |
| JP | 2014003801 | 1/2014 |
| KR | 10-2010-0125963 | 12/2010 |
| KR | 10-2010-0125964 | 12/2010 |
| KR | 10-2011-0035081 | 4/2011 |
| KR | 10-2012-0090832 | 8/2012 |

* cited by examiner

*Primary Examiner* — Nguyen Tran (57) ABSTRACT

A multi-synchronization power supply and an ultrasound system with the same are disclosed. The multi-synchronization power supply includes a microprocessor configured to receive frequency information indicative of a plurality of frequencies and to output a control signal based on the frequency information; a clock signal generating unit configured to receive a reference synchronization clock signal and to generate a plurality of synchronization clock signals corresponding to the plurality of frequencies by frequency-dividing the reference synchronization clock signal based on the control signal; and a plurality of DC-DC converters configured to receive the plurality of synchronization clock signals and a reference DC voltage, and to generate a plurality of DC voltages from the reference DC voltage based on the plurality of synchronization clock signals.

8 Claims, 5 Drawing Sheets

FIG. 1

| Ultrasound probe | Diagnosis mode | Frequency |
|---|---|---|
| Ultrasound probe A | B mode | DC-DC Converter#1: 000Hz<br>DC-DC Converter#2: 000Hz<br>⋮<br>DC-DC Converter#N: 000Hz |
| | C mode | DC-DC Converter#1: 000Hz<br>DC-DC Converter#2: 000Hz<br>⋮<br>DC-DC Converter#N: 000Hz |
| | D mode | DC-DC Converter#1: 000Hz<br>DC-DC Converter#2: 000Hz<br>⋮<br>DC-DC Converter#N: 000Hz |
| | CW mode | DC-DC Converter#1: 000Hz<br>DC-DC Converter#2: 000Hz<br>⋮<br>DC-DC Converter#N: 000Hz |
| Ultrasound probe B | B mode | DC-DC Converter#1: 000Hz<br>DC-DC Converter#2: 000Hz<br>⋮<br>DC-DC Converter#N: 000Hz |
| | C mode | DC-DC Converter#1: 000Hz<br>DC-DC Converter#2: 000Hz<br>⋮<br>DC-DC Converter#N: 000Hz |
| | D mode | DC-DC Converter#1: 000Hz<br>DC-DC Converter#2: 000Hz<br>⋮<br>DC-DC Converter#N: 000Hz |
| | CW mode | DC-DC Converter#1: 000Hz<br>DC-DC Converter#2: 000Hz<br>⋮<br>DC-DC Converter#N: 000Hz |
| ⋮ | ⋮ | ⋮ |

MULTI-SYNCHRONIZATION POWER SUPPLY AND ULTRASOUND SYSTEM WITH SAME

BACKGROUND

The present disclosure relates to a multi-synchronization power supply and an ultrasound system with the same.

SUMMARY

An ultrasound system has been widely used in medical fields to obtain information in a target object due to its non-invasive and non-destructive nature. Due to such characteristics of the ultrasound system, the ultrasound system can provide users with high-resolution images of the target object in real time without requiring an invasive surgical operation on the target object. Therefore, the ultrasound system has become an important tool for effectively diagnosing various diseases in medical fields.

The ultrasound system includes an ultrasound diagnosis device for providing an ultrasound image of a target object by transmitting ultrasound signals to the target object and receiving ultrasound signals reflected from the target object (i.e., ultrasound echo signals), and a power supply for generating a plurality of DC voltages and applying the plurality of DC voltages to the ultrasound diagnosis device. The power supply includes a plurality of DC-DC converters for generating the plurality of DC voltages based on a synchronization clock signal.

The DC-DC converters of the power supply generate a plurality of DC voltages needed for driving the ultrasound diagnosis device using a single synchronization clock signal having a predetermined frequency. The DC voltages generated by the single synchronization clock signal include pulse width modulation (PWM) switching noise components. Harmonic wave components may be generated by the PWM switching noise components, and the generated harmonic wave components may be generated as noise in ultrasound images depending on ultrasound probes or diagnosis modes.

The present disclosure provides a multi-synchronization power supply configured to generate a plurality of synchronization clock signals depending on at least one of ultrasound probes or diagnosis modes and to generate a plurality of DC voltages based on the plurality of generated synchronization clock signals, and an ultrasound system with the same.

According to one embodiment, a multi-synchronization power supply includes: a microprocessor configured to receive frequency information indicative of a plurality of frequencies and to output a control signal based on the frequency information; a clock signal generating unit configured to receive a reference synchronization clock signal and to generate a plurality of synchronization clock signals corresponding to the plurality of frequencies by frequency-dividing the reference synchronization clock signal based on the control signal; and a plurality of DC-DC converters configured to receive the plurality of synchronization clock signals and a reference DC voltage, and to generate a plurality of DC voltages from the reference DC voltage based on the plurality of synchronization clock signals.

In one embodiment, the frequency information includes the plurality of frequencies in one-to-one correspondence with the plurality of DC-DC converters.

In one embodiment, the microprocessor is configured to generate the control signal for sequentially generating the plurality of synchronization clock signals based on the frequency information.

In one embodiment, each of the plurality of DC-DC converters includes: a controller configured to generate a pulse signal for controlling generation of a DC voltage among the plurality of DC voltages, based on a synchronization clock signal among the plurality of synchronization clock signals; and a control switch configured to generate the DC voltage from the reference DC voltage based on the pulse signal.

In one embodiment, each of the plurality of DC-DC converters further includes a low pass filter for filtering the DC voltage.

In one embodiment, the multi-synchronization power supply further includes a reference DC voltage generating unit configured to generate the reference DC voltage from an input power source.

According to another embodiment, an ultrasound system includes: the multi synchronization power supply according to the one embodiment, and an ultrasound diagnosis device configured to be driven by the plurality of DC voltages generated by the multi-synchronization power supply and to provide the multi-synchronization power supply with the reference synchronization clock signal and the frequency information.

In another embodiment, the ultrasound diagnosis device includes: a control unit configured to generate the frequency information based on at least one of ultrasound probes or diagnosis modes; and a reference synchronization clock signal generating unit configured to generate the reference synchronization clock signal.

According to the present disclosure, a plurality of synchronization clock signals may be generated depending on at least one of ultrasound probes or diagnosis modes, so that noise components (PWM switching noise components) of a DC voltage generated by the power supply can be reduced.

Further, according to the present disclosure, the power supply generates a plurality of DC voltages using the plurality of synchronization clock signals, so that it is possible to easily find the noise components (PWM switching noise components) which affect an ultrasound image by a specific frequency of a synchronization clock signal depending on at least one of ultrasound probes or diagnosis modes.

Moreover, according to the present disclosure, when the ultrasound system should support a new ultrasound probe, the noise components (PWM switching noise components) generated by a specific frequency of a synchronization clock signal can be efficiently removed or reduced without an adaptation of hardware.

DETAILED DESCRIPTION

Embodiments of the present disclosure are illustrated for describing the technical spirit of the present disclosure. The scope of the claims according to the present disclosure is not limited to the embodiments described below or to detailed descriptions of these embodiments.

All technical or scientific terms used herein have meanings that are generally understood by a person having ordinary knowledge in the art to which the present disclosure pertains, unless otherwise specified. The terms used herein are selected for only more clear illustration of the present disclosure, and are not intended to limit the scope of claims in accordance with the present disclosure.

The expressions "include", "provided with", "have" and the like used herein should be understood as open-ended terms connoting the possibility of inclusion of other embodiments, unless otherwise mentioned in a phrase or sentence including the expressions.

A singular expression can include meanings of plurality, unless otherwise mentioned, and the same is applied to a singular expression stated in the claims.

The terms "first", "second", etc. used herein are used to identify a plurality of components from one another, and are not intended to limit the order or importance of the relevant components.

The term "unit" used in these embodiments means a software component or hardware component, such as a field-programmable gate array (FPGA) and an application specific integrated circuit (ASIC). However, a "unit" is not limited to software and hardware, it may be configured to be an addressable storage medium or may be configured to run on one or more processors. For example, a "unit" may include components, such as software components, object-oriented software components, class components, and task components, as well as processors, functions, attributes, procedures, subroutines, segments of program codes, drivers, firmware, micro-codes, circuits, data, databases, data structures, tables, arrays, and variables. Functions provided in components and "unit" may be combined into a smaller number of components and "units" or further subdivided into additional components and "units."

The expression "based on" used herein is used to describe one or more factors that influences a decision, an action of judgment or an operation described in a phrase or sentence including the relevant expression, and this expression does not exclude additional factors influencing the decision, the action of judgment or the operation.

When a certain component is described as "coupled to" or "connected to" another component, this should be understood as having meaning that the certain component may be coupled or connected directly to the other component or that the certain component may be coupled or connected to the other component via a new intervening component.

Hereinafter, embodiments of the present disclosure will be described with reference to the accompanying drawings. In the accompanying drawings, like or relevant components are indicated by like reference numerals. In the following description of embodiments, repeated descriptions of the identical or relevant components will be omitted. However, even if a description of a component is omitted, such a component is not intended to be excluded in an embodiment.

The term "target object" used herein may be an object or a subject of which an ultrasound image is obtained using an ultrasound system, and may be a biological object or inanimate object. In addition, if the target object is a biological object, the target object may mean a part of a human body, and a fetus or an organ such as liver, heart, uterus, brain, breast, abdomen, blood vessel (or blood flow) may be included in the target object, and any one section through the human body may be included in the target object. In addition, a "user" mentioned herein indicates medical professionals capable of operating and using the ultrasound system, and may be doctors, nurses, medical technologists, sonographers or other medical image experts, but is not limited thereto.

Figure 1:
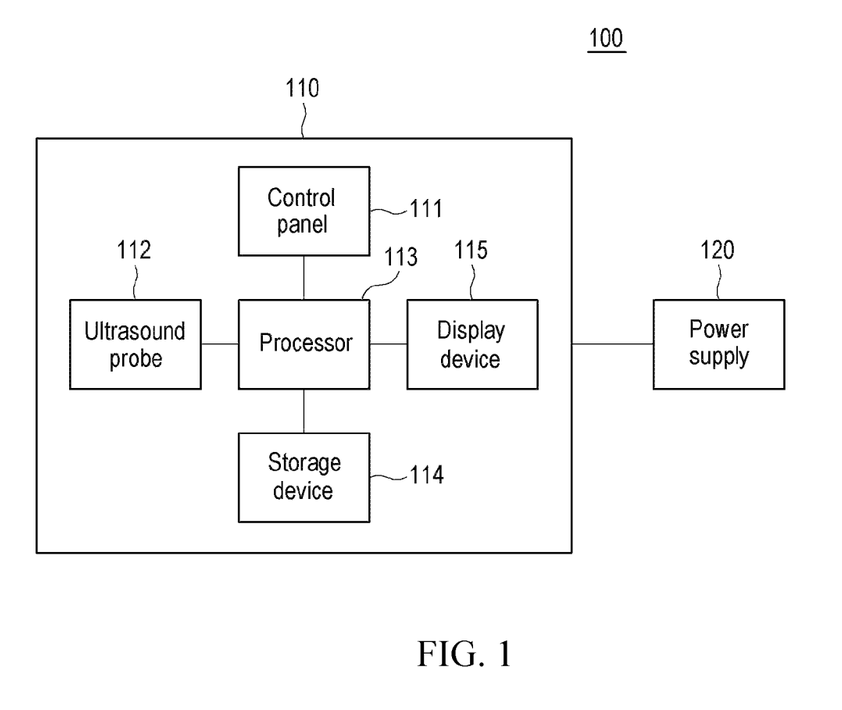
FIG. 1 is a block diagram schematically showing a configuration of an ultrasound system according to an embodiment of the present disclosure.

FIG. 1 is a block diagram schematically showing a configuration of an ultrasound system according to an embodiment of the present disclosure. Referring to FIG. 1, the ultrasound system 100 includes an ultrasound diagnosis device 110 and a power supply 120.

The ultrasound diagnosis device 110 transmits ultrasound signals to a target object, receives ultrasound signals (i.e., ultrasound echo signals) reflected from the target object, and provides an ultrasound image of the target object based on the received ultrasound echo signals. In the embodiment, the ultrasound diagnosis device 110 includes a control panel 111, an ultrasound probe 112, a processor 113, a storage device 114, and a display device 115.

The control panel 111 receives input information from a user and transmits the received input information to the processor 113. The control panel 111 may include an input device (not shown), which allows the user to interface with the ultrasound diagnosis device 110. The input device may include one of various input devices that are suitable for selecting diagnosis modes, controlling diagnosis operations, inputting suitable commands for diagnosis, controlling signal processing, controlling output of ultrasound images, etc. For example, the input devices include a trackball, a mouse, a keyboard, buttons, a stylus pen, a display such as a touch screen that enables input of commands, etc. However, the input device may include at least one of the input devices which are not limited to the foregoing.

In one embodiment, the control panel 111 receives input information (hereinafter, referred to as "first input information") for selecting an ultrasound probe 112, from the user. Further, the control panel 111 receives input information (hereinafter, referred to as "second input information") for selecting a diagnosis mode, from the user.

The ultrasound probe 112 receives electrical signals (hereinafter, referred to as "transmission signals") for obtaining an ultrasound image of a target object, from the processor 113. Further, the ultrasound probe 112 transforms the received transmission signals into ultrasound signals and transmits the transformed ultrasound signals to the target object. Further, the ultrasound probe 112 receives ultrasound signals (i.e., ultrasound echo signals) reflected from the target object and transforms the received ultrasound echo signals into electrical signals (hereinafter, referred to as "reception signals"). For example, the ultrasound probe 112 may include a convex probe, a linear probe or the like.

The processor 113 controls the ultrasound probe 112 to transmit the ultrasound signals to the target object and receive ultrasound echo signals reflected from the target object, based on the input information received via the control panel 111. Further, the processor 113 generates one or more ultrasound images of the target object based on the reception signals provided from the ultrasound probe 112. Further, the processor 113 generates frequency information indicative of a plurality of frequencies, and a reference synchronization clock signal. The frequency information and the reference synchronization clock signal will be described below in detail.

In one embodiment, the processor 113 controls operations of the control panel 111, the ultrasound probe 112, the storage device 114, the display device 115, and the power supply 120.

In one embodiment, the processor 113 may include a central processing unit (CPU), a field-programmable gate array (FPGA), an application specific integrated circuit (ASIC), etc. that can execute the control operations or program commands for executing such control operations. However, the processor 113 may not be limited thereto.

The storage device 114 stores the reception signals generated by the ultrasound probe 112. Further, the storage device 114 stores the ultrasound image generated by the processor 113. Further, the storage device 114 stores program commands for operating the ultrasound diagnosis device 110 and the power supply 120.

Figure 2:
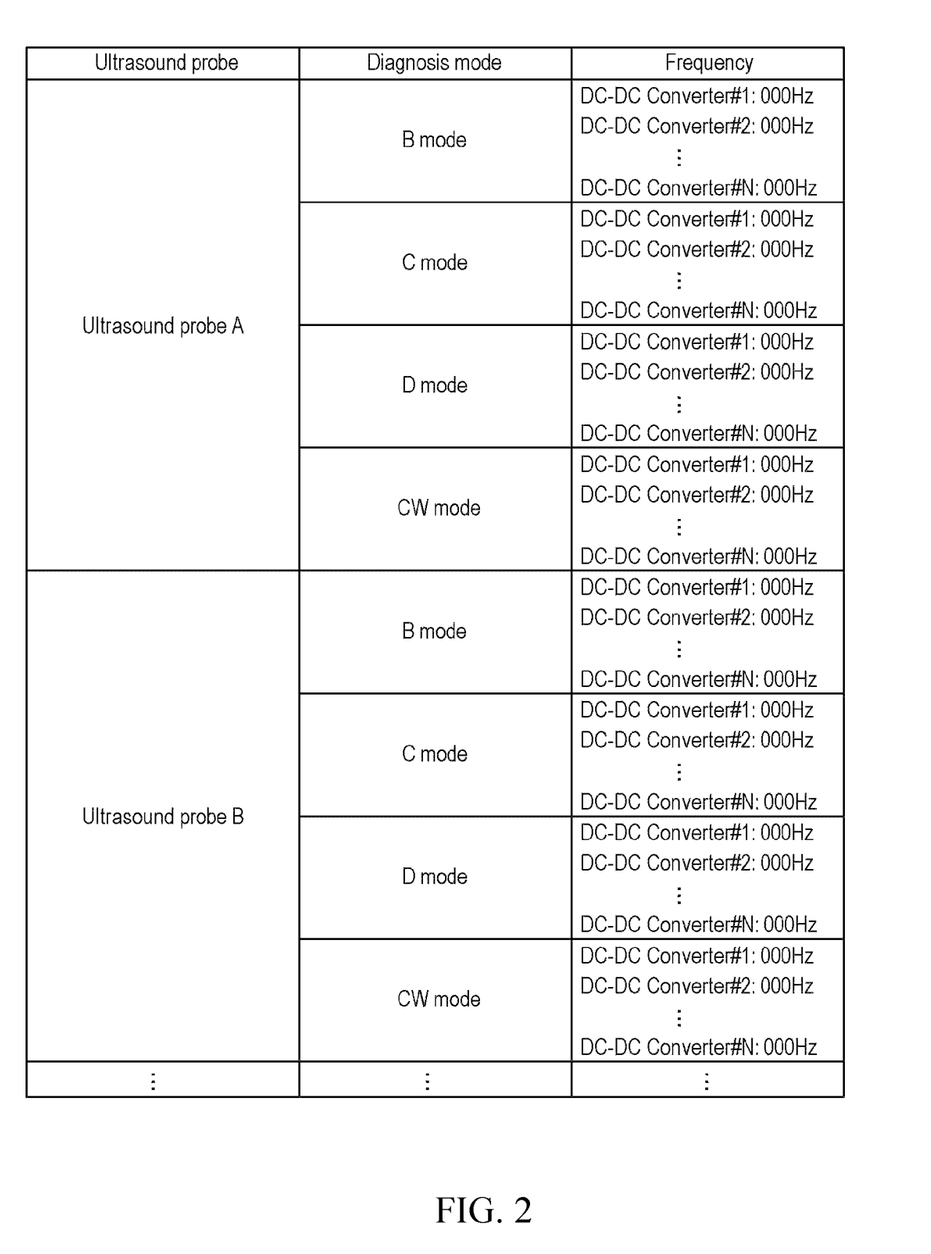
FIG. 2 is an illustrative view showing a database according to an embodiment of the present disclosure.

In one embodiment, the storage device 114 stores a plurality of frequencies corresponding to a plurality of diagnosis modes for each ultrasound probe in a database as shown in FIG. 2. The frequency represents a frequency of a synchronization clock signal input into a DC-DC converter described below. Further, the plurality of frequencies stored in the storage device 114 may be frequencies determined by preliminary experiments or the like.

In one embodiment, the storage device 114 may include a magnetic disk (e.g., magnetic tape, flexible disk, hard disk, etc.), an optical disk (e.g., CD, DVD, etc.), a semiconductor memory (e.g., USB memory, memory card, etc.) and the like. However, the storage device 114 may not be limited thereto.

The display device 115 displays the ultrasound image generated by the processor 113. Further, the display device 115 may display information on the ultrasound image, operation states of the ultrasound diagnosis device 110 or the power supply 120.

In one embodiment, the display device 115 may include a liquid crystal display (LCD), a light emitting diode (LED) display, a thin film transistor-liquid crystal display (TFT-LCD), an organic light-emitting diode (OLED) display, a flexible display, or the like. However, the display device 115 may not be limited thereto.

The power supply 120 generates a plurality of DC voltages, based on the reference synchronization clock signal and the frequency information provided from the ultrasound diagnosis device 110. The power supply 120 supplies the plurality of generated DC voltages to the ultrasound diagnosis device 110. Therefore, the ultrasound diagnosis device 110 is driven by the plurality of DC voltages supplied from the power supply 120.

Figure 3:
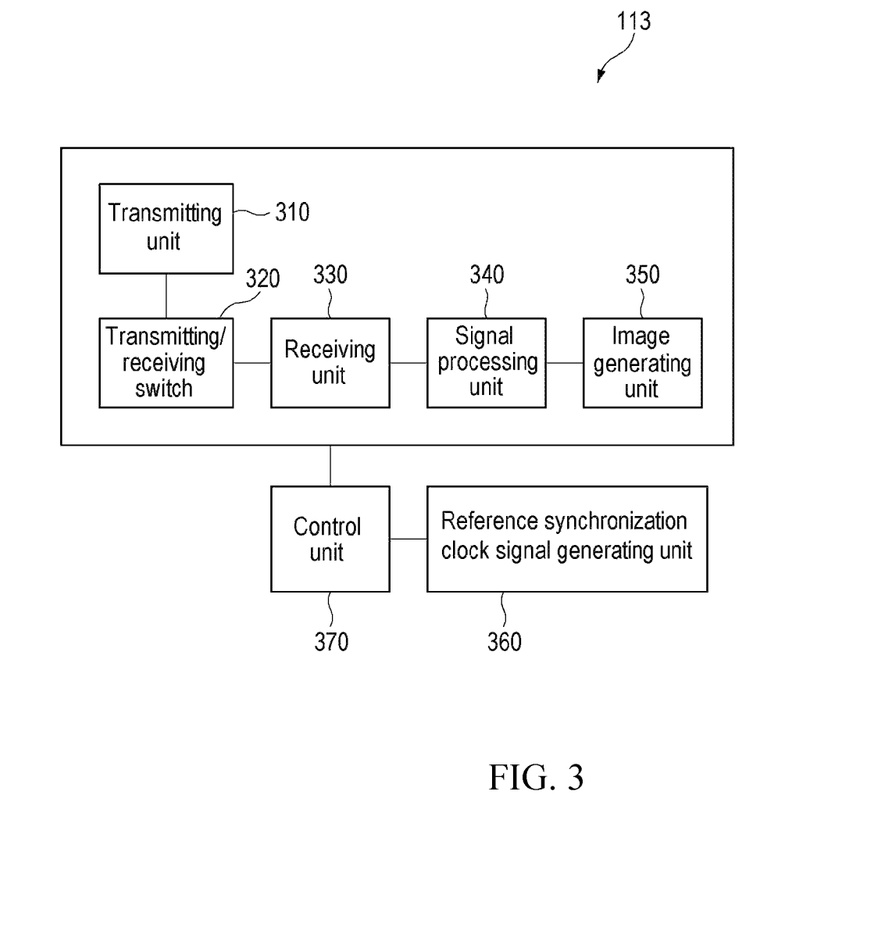
FIG. 3 is a block diagram schematically showing a configuration of a processor according to an embodiment of the present disclosure.

FIG. 3 is a block diagram schematically showing a configuration of the processor 113 according to an embodiment of the present disclosure. Referring to FIG. 3, the processor 113 includes a transmitting unit 310. The transmitting unit 310 generates transmission signals for obtaining an ultrasound image of the target object. The transmitting section 310 provides the generated transmission signals to the ultrasound probe 120. The ultrasound probe 120 transforms the received transmission signals into the ultrasound signals and transmits the transformed ultrasound signals to the target object. Further, the ultrasound probe 120 receives the ultrasound echo signals reflected from the target object to generate the reception signals.

The processor 113 further includes a transmitting/receiving switch 320 and a receiving unit 330. The transmitting/receiving switch 320 may switch between the transmitting unit 310 and the receiving unit 330. For example, the transmitting/receiving switch 320 may include a duplexer. In one embodiment, the transmitting/receiving switch 320 can electrically connect one of the transmitting unit 310 and the receiving unit 330 to the ultrasound probe 120 when the ultrasound probe 120 alternately performs reception of the transmission signals from the transmitting unit 310 and reception of the ultrasound echo signals reflected from the target object.

The receiving unit 330 amplifies the reception signals that are received via the transmitting/receiving switch 320 from the ultrasound probe 120. Further, the receiving unit 330 generates digital signals by performing analog-to-digital conversion on the amplified reception signals. In one embodiment, the receiving unit 330 includes a time gain compensation (TGC) unit (not shown) for compensating for attenuation generated typically when the ultrasound signals pass through the target object, and an analog-to-digital conversion unit (not shown) for converting the analog signals into the digital signals.

The processor 113 further includes a signal processing unit 340. The signal processing unit 340 performs a signal process (e.g., beamforming) on the digital signals provided from the receiving unit 330 to generate receive-focused signals. Further, the signal processing unit 340 generates ultrasound data based on the receive-focused signals. The ultrasound data may include radio frequency (RF) data, in-phase/quadrature (RF) data or the like.

The processor 113 further includes an image generating unit 350. The image generating unit 350 generates one or more ultrasound images of the target object based on the ultrasound data provided from the signal processing unit 340. The ultrasound images include a brightness mode (B-mode) image, a color flow mode (C-mode) image, a spectral Doppler mode (D-mode) image, a continuous wave mode (CW-mode) image, or the like.

The processor 113 further includes a reference synchronization clock signal generating unit 360. The reference synchronization clock signal generating unit 360 generates the reference synchronization clock signal having a predetermined frequency. For example, the predetermined frequency may be several MHz to several tens of MHz. However, the predetermined frequency may not be limited thereto.

The processor 113 further includes a control unit 370. The control unit 370 generates the frequency information indicative of the plurality of frequencies based on at least one of ultrasound probes and diagnosis modes. For example, the frequency information includes a plurality of frequencies in one-to-one correspondence with a plurality of DC-DC converters 440_1 to 440_N described below (see FIG. 4). Further, the control unit 370 controls operations of the transmitting unit 310, the transmitting/receiving switch 320, the receiving unit 330, the signal processing unit 340, the image generating unit 350, and the reference synchronization clock signal generating unit 360.

In one embodiment, the control unit 370 receives input information provided from the control panel 111, queries the storage device 114 based on the received input information, and extracts a plurality of frequencies corresponding to the input information. For example, based on the first input information regarding selection of "ultrasound probe A" as the ultrasound probe 112 and the second input information regarding selection of "B mode" as the diagnosis mode, the control unit 370 extracts a plurality of frequencies corresponding to "ultrasound probe A" and "B mode" from the storage device 114. Further, the control unit 370 generates frequency information indicative of the plurality of extracted frequencies. That is, the control unit 370 generates the frequency information including the plurality of frequencies (i.e., plurality of extracted frequencies) in one-to-one correspondence with the plurality of DC-DC converters 440_1 to 440_N (see FIG. 4).

Figure 4:
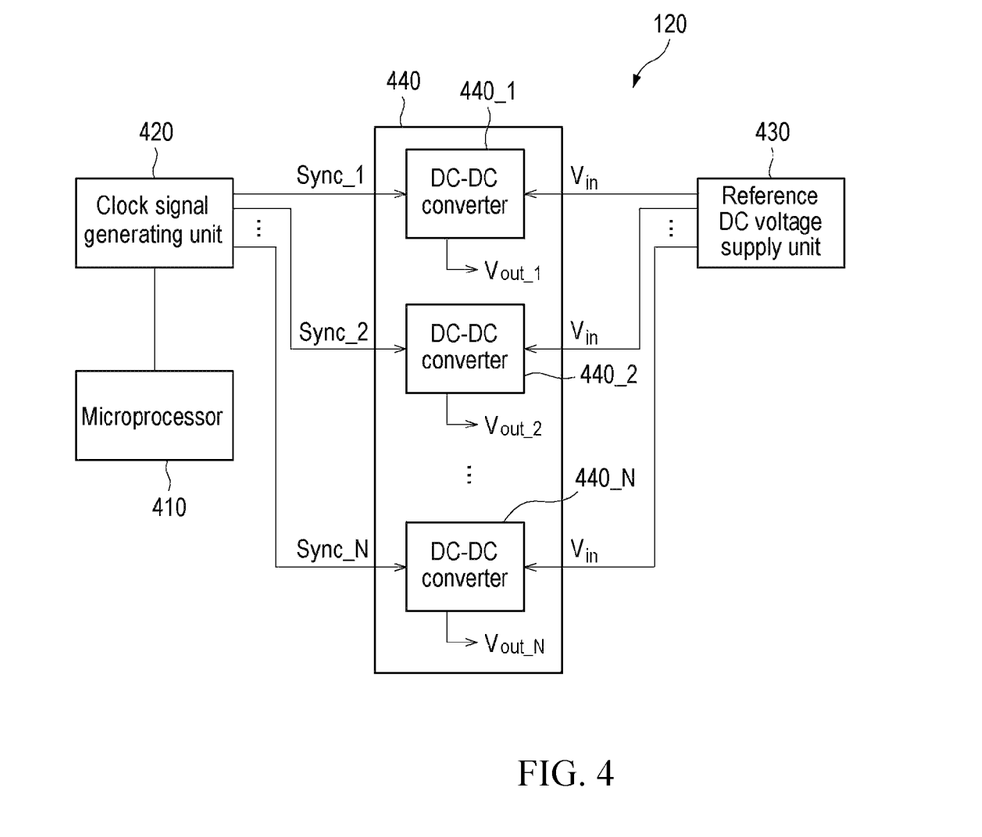
FIG. 4 is a block diagram schematically showing a configuration of a power supply according to an embodiment of the present disclosure.

FIG. 4 is a block diagram schematically showing a configuration of the power supply 120 according to an embodiment of the present disclosure. Referring to FIG. 4, the power supply 120 includes a microprocessor 410. The microprocessor 410 receives the frequency information from the control unit 370 and outputs a control signal based on the received frequency information. For example, the microprocessor 410 generates a control signal for sequentially generating a plurality of synchronization clock signals based on the frequency information.

Figure 5:
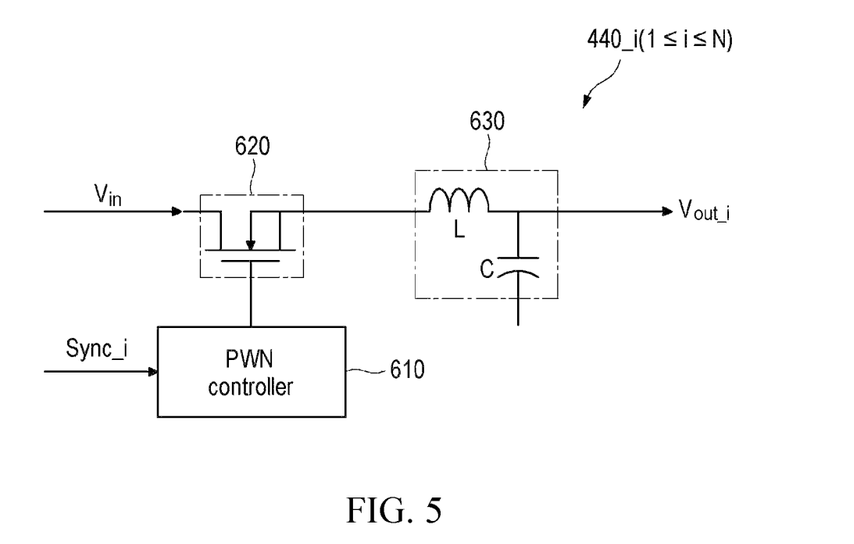
FIG. 5 is an illustrative view showing a reference synchronization clock signal and a plurality of synchronization clock signals according to an embodiment of the present disclosure.

In one embodiment, the microprocessor 410 outputs a control signal for sequentially generating a plurality of synchronization clock signals Sync_1 to Sync_N from the reference synchronization clock signal Sync_ref, as shown in FIG. 5, based on the frequency information. For example, the reference synchronization clock signal Sync_ref has a frequency higher than those of the plurality of synchronization clock signals Sync_1 to Sync_N.

The power supply 120 further includes a clock signal generating unit 420. The clock signal generating unit 420 receives the control signal provided from the microprocessor 410 and receives the reference synchronization clock signal from the reference synchronization clock signal generating unit 360 of the processor 113. Further, the clock signal generating unit 420 generates a plurality of synchronization clock signals corresponding to the plurality of frequencies by frequency-dividing the reference synchronization clock signal based on the control signal. For example, as shown in FIG. 5, the clock signal generating unit 420 sequentially generates a plurality of synchronization clock signals Sync_1 to Sync_N corresponding to the plurality of frequencies by frequency-dividing the reference synchronization clock signal Sync_ref.

The power supply 120 further includes a reference DC voltage supply unit 430. The reference DC voltage supply unit 430 generates at least one reference DC voltage Vin using an input power source from the outside. As an example, the reference DC voltage supply unit 430 generates a plurality of reference DC voltages Vin having an identical voltage value. As another example, the reference DC voltage supply unit 430 generates a plurality of reference DC voltages Vin having different voltage values.

The power supply 120 further includes a voltage regulator 440. The voltage regulator 440 receives the plurality of synchronization clock signals from the clock signal generating unit 420 and receives the reference DC voltage Vin from the reference DC voltage supply unit 430. Further, the voltage regulator 440 generates a plurality of DC voltages Vout_1 to Vout_N from the reference DC voltage Vin based on the plurality of synchronization clock signals. In one embodiment, the voltage regulator 440 may include the plurality of DC-DC converters 440_1 to 440_N.

Figure 6:
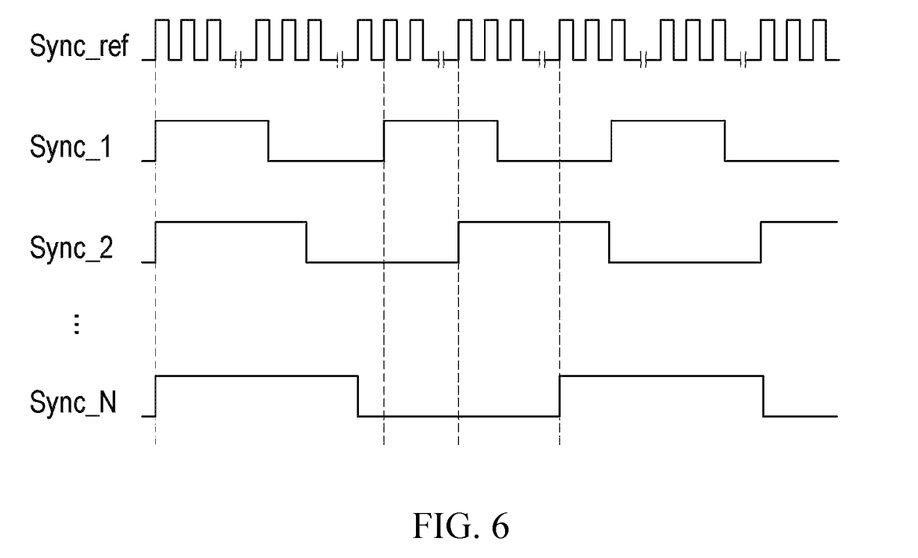
FIG. 6 is a block diagram schematically showing a configuration of a DC-DC converter according to an embodiment of the present disclosure.

In one embodiment, the DC-DC converter 440_i ($1 \leq i \leq N$) includes a pulse width modulation (PWM) controller 610 as shown in FIG. 6. The PWM controller 610 receives a synchronization clock signal Sync_i ($1 \leq i \leq N$) among the plurality of synchronization clock signals Sync_1 to Sync_N, and generates a pulse signal for controlling generation of a DC voltage Vout_i ($1 \leq i \leq N$) among the plurality of DC voltages Vout_1 to Vout_N based on the received synchronization clock signal Sync_i ($1 \leq i \leq N$). For example, the pulse signal may have the same frequency as the synchronization clock signal Sync_i ($1 \leq i \leq N$).

The DC-DC converter 440_i ($1 \leq i \leq N$) further includes a control switch 620. The control switch 620 generates a DC voltage Vout_i ($1 \leq i \leq N$) among the plurality of DC voltages Vout_1 to Vout_N from the reference DC voltage Vin provided from the reference DC voltage supply unit 430, based on the pulse signal provided from the PWM controller 610.

The DC-DC converter 440_i ($1 \leq i \leq N$) further includes a low pass filter 630. The low pass filter 630 filters the DC voltage Vout_i ($1 \leq i \leq N$) generated by the control switch 620. For example, the low pass filter 630 includes a LC filter. However, the low pass filter 630 may not be limited thereto.

Although the technical spirit of the present disclosure has been described by the examples described in some embodiments and illustrated in the accompanying drawings, it should be noted that various substitutions, modifications, and changes can be made without departing from the scope of the present disclosure which can be understood by those skilled in the art to which the present disclosure pertains. In addition, it should be noted that that such substitutions, modifications and changes are intended to fall within the scope of the appended claims.

What is claimed:

1. A multi-synchronization power supply comprising:
    a microprocessor configured to receive frequency information indicative of a plurality of frequencies and to output a control signal based on the frequency information;
    a clock signal generating unit configured to receive a reference synchronization clock signal and to generate a plurality of synchronization clock signals corresponding to the plurality of frequencies by frequency-dividing the reference synchronization clock signal based on the control signal; and
    a plurality of DC-DC converters configured to receive the plurality of synchronization clock signals and a reference DC voltage, and to generate a plurality of DC voltages from the reference DC voltage based on the plurality of synchronization clock signals.

2. The multi-synchronization power supply of claim 1, wherein the frequency information comprises the plurality of frequencies in one-to-one correspondence with the plurality of DC-DC converters.

3. The multi-synchronization power supply of claim 2, wherein the microprocessor is configured to generate the control signal for sequentially generating the plurality of synchronization clock signals based on the frequency information.

4. The multi-synchronization power supply of claim 1, wherein each of the plurality of DC-DC converters comprises:
    a controller configured to generate a pulse signal for controlling generation of a DC voltage among the plurality of DC voltages, based on a synchronization clock signal among the plurality of synchronization clock signals; and
    a control switch configured to generate the DC voltage from the reference DC voltage based on the pulse signal.

5. The multi-synchronization power supply of claim 1, wherein each of the plurality of DC-DC converters further comprises a low pass filter for filtering the DC voltage.

6. The multi-synchronization power supply of claim 1, further comprising a reference DC voltage generating unit configured to generate the reference DC voltage from an input power source.

7. An ultrasound system comprising:
   the multi-synchronization power supply according to claim 1,
   an ultrasound diagnosis device configured to be driven by the plurality of DC voltages generated by the multi-synchronization power supply and to provide the multi-synchronization power supply with the reference synchronization clock signal and the frequency information.

8. The ultrasound system of claim 7, wherein the ultrasound diagnosis device comprises:
   a control unit configured to generate the frequency information based on at least one of ultrasound probes or diagnosis modes; and
   a reference synchronization clock signal generating unit configured to generate the reference synchronization clock signal.

* * * * *